United States Patent [19]

Kompis et al.

[11] 4,137,411
[45] Jan. 30, 1979

[54] PREPARATION OF 2,4-DIAMINO-5-(4-AMINO-3,5-SUBSTITUTED-BENZYL)-PYRIMIDINES

[75] Inventors: Ivan Kompis, Oberwil; Alexander E. Wick, Riehen, both of Switzerland

[73] Assignee: Hoffmann-La Roche Inc., Nutley, N.J.

[21] Appl. No.: 874,133

[22] Filed: Feb. 1, 1978

[30] Foreign Application Priority Data

Feb. 4, 1977 [CH] Switzerland .................. 1383/77

[51] Int. Cl.² ........................................ C07D 239/48
[52] U.S. Cl. ................................................ 544/325
[58] Field of Search ........................................ 544/325

[56] References Cited

U.S. PATENT DOCUMENTS

| 3,849,407 | 11/1974 | Cresswell et al. | 544/325 |
| 3,931,181 | 1/1976 | Kompis et al. | 544/325 |
| 4,008,236 | 2/1977 | Perun et al. | 544/325 |

FOREIGN PATENT DOCUMENTS 957797  5/1964  United Kingdom .................. 544/325

OTHER PUBLICATIONS

Kompis et al., Chemical Abstracts, 83:43376h (1975).

*Primary Examiner*—Paul M. Coughlan, Jr.
*Attorney, Agent, or Firm*—Jon S. Saxe; George M. Gould; William G. Isgro

[57] ABSTRACT

A benzylpyrimidines of the formula

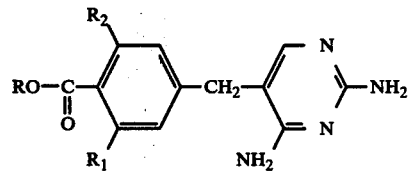

wherein $R^1$ and $R^2$ independently are $C_{1-3}$-alkyl or $C_{1-3}$-alkoxy, and R is hydrogen or lower alkyl, is treated with hydroxylamine or a salt thereof in polyphosphoric acid or alternatively, when R is hydrogen, is treated with sodium azide in polyphosphoric acid, to yield the corresponding 4-amino benzylpyrimidine.

8 Claims, No Drawings

PREPARATION OF 2,4-DIAMINO-5-(4-AMINO-3,5-SUBSTITUTED-BENZYL)-PYRIMIDINES

BRIEF SUMMARY OF THE INVENTION

The invention relates to a process which comprises reacting a compound of the formula

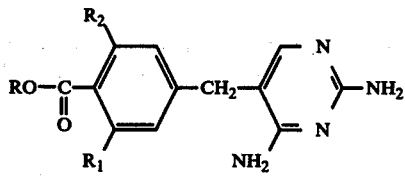

II wherein R, $R^1$ and $R^2$ are as herein described, with hydroxylamine or a salt thereof in polyphosphoric acid, to yield the corresponding 4-amino compound.

In another aspect the invention relates to a process which comprises reacting a compound of the formula

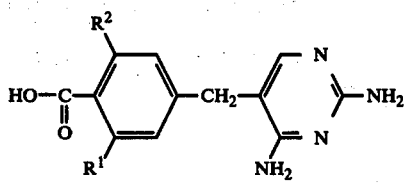

III wherein $R^1$ and $R^2$ are as herein described, with sodium azide in polyphosphoric acid.

DETAILED DESCRIPTION OF THE INVENTION

The benzylpyrimidines obtained according to the present invention have the formula

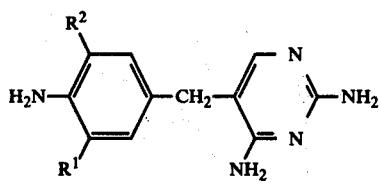

I wherein $R^1$ and $R^2$, independently, are a $C_{1-3}$-alkyl or $C_{1-3}$-alkoxy group.

More specifically, the benzylpyrimidines of formula I are prepared according to the invention by:

(a) reacting a compound of the formula

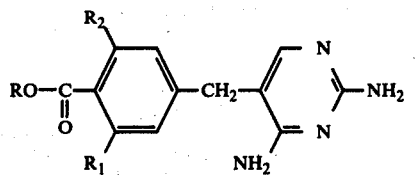

II wherein $R^1$ and $R^2$ are as herein described and R is hydrogen or lower alkyl, with hydroxylamine or a salt thereof in polyphosphoric acid, or (b) reacting a compound of the formula

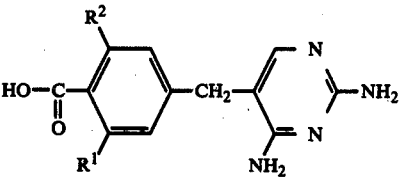

III wherein $R^1$ and $R^2$ are as herein described, with sodium azide in polyphosphoric acid.

The benzylpyrimidines of formula I are known compounds which are valuable antibacterial agents or potentiate the antibacterial activity of sulfonamides. 2,4-Diamino-5-(4-amino-3,5-dimethoxybenzyl)-pyrimidine is a particularly interesting benzylpyrimidine of formula I. It has, however, been shown that the previously described processes for the preparation of the benzylpyrimidines of formula I, as for example, in German Offenlegungsschrift No. 2,443,682, are less suitable for use on a commercial scale, since, for example, the required starting materials are relatively inaccessible or expensive. The present invention overcomes these problems and enables the benzylpyrimidines of formula I to be prepared on a commercial scale in a simple and economical manner.

In a preferred aspect of embodiment (a) of the invention, a compound of formula II is reacted with a hydroxylamine salt in polyphosphoric acid. Particularly suitable hydroxylamine salts are the salts mentioned in the examples which follow. Surprisingly, it has been found that this embodiment yields the benzylpyrimidines of formula I in high yield and purity under mild conditions, for instance, at 60° to 80° C. Accordingly, this embodiment is preferably carried out at a temperature in the range of from about 60° to about 80° C. A methyl ester of formula II is conveniently used as the starting material. The preparation of the esters of formula II is described in German Offenlegungsschrift No. 2,435,934. The acids of formula II can be prepared by saponifying the esters of formula II, for example, with aqueous-alcoholic bases.

In embodiment (b) of the invention, a compound of formula III is reacted with sodium azide in polyphosphoric acid. The reaction is conveniently carried out with slight warming. A starting material of formula III can be prepared from an ester of formula II as described in the preceding paragraph.

The Examples which follow further illustrate the invention:

EXAMPLE 1

Preparation of 2,4-diamino-5-(4-amino-3,5-dimethoxybenzyl)-pyrimidine.

0.75 g of sodium azide was added portionwise to a suspension of 3.04 g of α-(2,4-diamino-5-pyrimidinyl)-2,6-dimethoxy-p-tolylbenzoic acid in 23 g of polyphosphoric acid and 5 ml of chloroform. The stirred mixture was warmed at 40° C. for 30 minutes and at 45° C. for 2 hours. After cooling, 75 ml of water were added with stirring. The solution was filtered and adjusted to pH 10 with 28% sodium hydroxide solution. The precipitated product was removed by filtration under suction. Then it was suspended in water and stirred for 15 minutes. After filtration under suction, drying and recrystallization from methanol, there were obtained 1.8 g (65%) of 2,4-diamino-5-(4-amino-3,5-dimethoxybenzyl)-pyrimidine having a melting point of 213°–214° C.

EXAMPLE 2

Preparation of 2,4-diamino-5-(4-amino-2,5-dimethoxybenzyl)-pyrimidine.

A suspension of 304 mg of α-(2,4-diamino-5-pyrimidinyl)-2,6-dimethoxy-p-tolylbenzoic acid in 2.5 g of polyphosphoric acid and 100 mg of hydroxylamine sulfate was warmed at 80° C. for 45 minutes. After cooling, the mixture was treated with 5 ml of water and made alkaline with 28% sodium hydroxide solution. The resulting suspension was extracted with ethyl acetate. The ethyl acetate extracts were washed with water, dried and evaporated. After recrystallization from methanol, there were obtained 180 mg (65%) of 2,4-diamino-5-(4-amino-3,5-dimethoxybenzyl)-pyrimidine of melting point 213°–214° C.

EXAMPLE 3

Preparation of 2,4-diamino-5-(4-amino-3,5-diethoxybenzyl)-pyrimidine.

A suspension of 1.8 g of ethyl α-(2,4-diamino-5-pyrimidinyl)-2,6-diethoxy-p-tolylbenzoate and 0.5 g of hydroxylamine sulfate in 17 g of polyphosphoric acid was stirred at 75° C. for 1 hour. After cooling, 75 ml of water were added with stirring. The solution was filtered and the filtrate was adjusted to pH 10 with about 50 ml of 28% sodium hydroxide solution. The precipitated product was removed by filtration under suction, suspended in water, again removed by filtration under suction and dried. The yield was 1.18 g (78%). Recrystallization from methanol yielded 2,4-diamino-5-(4-amino-3,5-diethoxybenzyl)-pyrimidine having a melting point of 192°–194° C.

EXAMPLE 4

Preparation of 2,4-diamino-5-(4-amino-3,5-dimethoxybenzyl)-pyrimidine.

15.9 g of finely powdered methyl α-(2,4-diamino-5-pyrimidinyl)2,6-dimethoxy-p-tolylbenzoate were added at 25° C. to 150 g of polyphosphoric acid. In so doing, the temperature rose to about 35° C. The thick suspension was stirred for 15 minutes and treated with 4.2 g of hydroxylamine hydrochloride. The stirred mixture was immersed in an oil-bath, pre-warmed to 80° C., and warmed and stirred for 90 minutes. After cooling, 650 ml of deionized water were added with stirring. The solution was filtered and adjusted to pH 10 with about 320 ml of about 28% sodium hydroxide solution with cooling. The precipitated product was removed by filtration under suction, suspended in 100 ml of deionized water, again removed by filtration under suction and dried. The crude product was recrystallized from 280 ml of hot methanol and gave 11.5 g (83.5%) of 2,4-diamino-5-(4-amino-3,5-dimethoxybenzyl)-pyrimidine having a melting point of 209°–210° C.

We claim:

1. A process for the preparation of a benzylpyrimidine of the formula

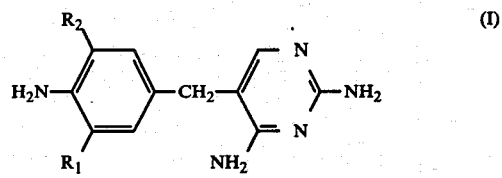

wherein $R^1$ and $R^2$ independently are $C_{1-3}$-alkyl or $C_{1-3}$-alkoxy, which comprises reacting a compound of the formula

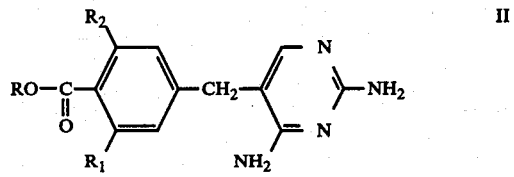

wherein $R^1$ and $R^2$ are as above and R is hydrogen or lower alkyl, with hydroxylamine or a salt thereof in polyphosphoric acid.

2. A process for the preparation of a benzylpyrimidine of the formula

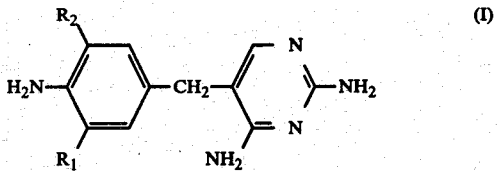

wherein $R^1$ and $R^2$, independently, are $C_{1-3}$-alkyl or $C_{1-3}$-alkoxy, which comprises reacting a compound of the formula

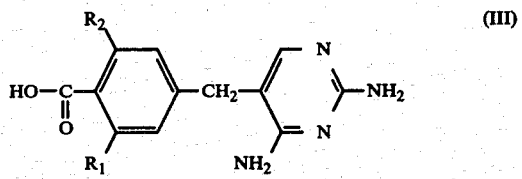

wherein $R^1$ and $R^2$ are as above, with sodium azide in polyphosphoric acid.

3. A process in accordance with claim 1, wherein the reaction is carried out at a temperature in the range of from about 60° to about 80° C.

4. A process in accordance with claim 2, wherein the reaction is carried out at a temperature in the range of from about 60° C. to about 80° C.

5. A process in accordance with claim 3, wherein $R^1$ and $R^2$ are methoxy.

6. A process in accordance with claim 4, wherein $R^1$ and $R^2$ are methoxy.

7. A process in accordance with claim 5, wherein R is hydrogen.

8. A process in accordance with claim 5, wherein R is lower alkyl.